(12) United States Patent
Zeng et al.

(10) Patent No.: US 12,402,908 B2
(45) Date of Patent: Sep. 2, 2025

(54) TRANSPERINEAL PUNCTURE GUIDING BRACKET

(71) Applicant: JingFang Precision Medical Device (Shenzhen) Co., Ltd., Guangdong (CN)

(72) Inventors: Junhua Zeng, Guangdong (CN); Yi Han, Guangdong (CN)

(73) Assignee: JingFang Precision Medical Device (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 18/836,353

(22) PCT Filed: May 12, 2023

(86) PCT No.: PCT/CN2023/093911
§ 371 (c)(1),
(2) Date: Aug. 7, 2024

(87) PCT Pub. No.: WO2024/066379
PCT Pub. Date: Apr. 4, 2024

(65) Prior Publication Data
US 2025/0152197 A1     May 15, 2025

(30) Foreign Application Priority Data
Sep. 27, 2022   (CN) .......................... 202211187742.0

(51) Int. Cl.
*A61B 17/34*     (2006.01)
*A61B 8/00*      (2006.01)
*A61B 8/12*      (2006.01)

(52) U.S. Cl.
CPC ............ *A61B 17/3403* (2013.01); *A61B 8/12* (2013.01); *A61B 8/4455* (2013.01); *A61B 2017/3411* (2013.01); *A61B 2017/3413* (2013.01)

(58) Field of Classification Search
None
See application file for complete search history.

(56) References Cited

U.S. PATENT DOCUMENTS

| | | | |
|---|---|---|---|
| 5,871,448 A * | 2/1999 | Ellard .................. | A61B 8/0841 600/459 |
| 2016/0022309 A1 * | 1/2016 | Allaway ............ | A61B 10/0241 600/464 |

(Continued)

FOREIGN PATENT DOCUMENTS

| | | |
|---|---|---|
| CN | 219126587 U | 6/2023 |
| JP | 2006075386 A | 3/2006 |

OTHER PUBLICATIONS

International Search Report of PCT Patent Application No. PCT/CN2023/093911 issued on Jul. 28, 2023.

*Primary Examiner* — Amal Aly Farag (57) ABSTRACT

A transperineal puncture guiding bracket is provided, comprising a probe fixing assembly and a guiding assembly, wherein a mounting plate is set on top of the probe fixing assembly, the guiding assembly comprises a needle grooved plate and a cover plate, and the needle grooved plate is detachably combined to a first side surface of the mounting plate by a first vertical insertion structure, a first hanging structure and a first buckling structure, the cover plate is detachably combined with the needle grooved plate by a second vertical insertion structure, a second hanging structure and a second buckling structure, thereby the cover plate is detachably attached to the needle grooved plate to form a plurality of needle guiding holes. In the bracket, needled grooved plates of different specifications can be replaced according to the puncture needles, and the puncture needle can be easily separated from the bracket.

10 Claims, 10 Drawing Sheets

(56) References Cited

U.S. PATENT DOCUMENTS

2018/0199851 A1\* 7/2018 Krieger ................ G01R 33/287
2022/0160339 A1 5/2022 Whitmore et al.

\* cited by examiner

TRANSPERINEAL PUNCTURE GUIDING BRACKET

FIELD

The present application generally relates to ultrasound intervention medical auxiliary devices, more particularly to a transperineal puncture guiding bracket.

BACKGROUND

With changes of people's lifestyle in recent years, an incidence rate of prostate cancer in China has increased year by year, and it has ranked first in malignant tumors of the urinary system (male). Early detection and timely treatment can save lives of patients. Real time ultrasound guided prostate biopsy is a best choice for diagnosing prostate cancers due to its small trauma and high accuracy. There are two ways to perform prostate biopsy surgery: one is through the perineum, and the other is through the rectum. During transrectal puncture biopsy surgery, a biopsy needle is inserted into the prostate site through an entrance of the anus and intestines, and the rectal mucosa is prone to bleeding and infection after surgery. During transperineal puncture biopsy surgery, a biopsy needle is inserted into the prostate site through the external perineum, thus the surgery can be aseptic, has a low risk of infection, comprehensive sampling, and higher safety. Transperineal puncture biopsy is more conducive to detecting early tumors and reducing postoperative adverse reactions, and is currently a mainstream prostate biopsy method.

In the process of transperineal prostate biopsy surgery, an intracavitary ultrasound probe is equipped with a puncture guiding bracket for use. A front end of the puncture guiding bracket needs to be close to a patient's perineum, and a biopsy needle needs to pass through a guide hole on the puncture guiding bracket to puncture into the prostate gland. Commonly used puncture guiding brackets currently have the following limitations: 1. Due to use of a closed needle hole structure for guiding a biopsy needle, the puncture guiding bracket cannot be separated from the biopsy needle, which limits the flexible operation of doctors. 2. A needle grooved plate and a bracket body are integrated to form a whole structure, thus different puncture guiding brackets are required when using biopsy needles of different specifications, which brings inconvenience to doctors during surgical operations.

SUMMARY

The technical problem to be solved by the present application is to provide a transperineal puncture guiding bracket that can replace needle grooved plates of different specification according to puncture needles of different specifications and facilitate separation of puncture needles in view of the above-mentioned drawbacks of the prior art.

The technical solution adopted by the present application to solve the technical problem thereof is to provide a transperineal puncture guiding bracket, comprising a probe fixing assembly and a guiding assembly, wherein the probe fixing assembly is fixedly installed with an intracavitary ultrasound probe, the guiding assembly provides a plurality of vertically distributed and parallel needle guiding holes along a puncture direction, wherein, an mounting plate is set on top of the probe fixing assembly, and the guiding assembly further comprises a needle grooved plate and a cover plate, the needle grooved plate has a first side surface and a second side surface opposite to the first side surface, with the first side surface of the needle grooved plate being provided with a plurality of vertically distributed and parallel needle guiding grooves; and a lower portion of the needle grooved plate is detachably combined with the top of the probe fixing assembly adjacent to the mounting plate by a first vertical insertion structure, an upper portion of the needle grooved plate is detachably hung with an upper portion of the mounting plate by a first hanging structure, and the second side surface of the needle grooved plate is detachably buckled with a first side surface of the mounting plate by a first buckling structure, thereby the second side surface of the needle grooved plate is detachably attached to the first side surface of the mounting plate; and a lower portion of the cover plate is detachably combined with the lower portion of the needle grooved plate or the top of the probe fixing assembly by a second vertical insertion structure, an upper portion of the cover plate is detachably hung with the upper portion of the needle grooved plate by a second hanging structure, and the cover plate is further detachably buckled with the upper portion of the mounting plate, the upper portion of the needle grooved plate or the top of the probe fixing assembly through a second buckling structure, thereby a second side surface of the cover plate is detachably attached to the first side surface of the needle grooved plate to close the plurality of needle guiding grooves to form the plurality of needle guiding holes.

In the transperineal puncture guiding bracket according to an embodiment of the present application, the first vertical insertion structure comprises first limiting feet provided at the lower portion of the needle grooved plate which extend out from the first side surface of the needle grooved plate and limiting grooves formed at the top of the probe fixing assembly for insertion of the first limiting feet; and the second vertical insertion structure comprises second limiting feet set at the lower portion of the cover plate and limiting holes on the first limiting feet of the needle grooved plate for insertion of the second limiting feet.

In the transperineal puncture guiding bracket according to an embodiment of the present application, the first vertical insertion structure comprises first limiting feet provided at the lower portion of the needle grooved plate and first limiting grooves set at the top of the probe fixing assembly for insertion of the first limiting feet; and the second vertical insertion structure comprises second limiting feet set at the lower portion of the cover plate and second limiting grooves formed at the top of the probe fixing assembly for insertion of the second limiting feet.

In the transperineal puncture guiding bracket according to an embodiment of the present application, the first hanging structure comprises first hanging holes at the upper portion of the needle grooved plate and first hooks at the upper portion of the mounting plate which extend out from the first side surface of the mounting plate to hang into the first hanging holes; and the second hanging structure comprises second hanging holes at the upper portion of the cover plate and second hooks at the upper portion which extend out from the first side surface of the needle grooved plate to hang into the second hanging holes.

In the transperineal puncture guiding bracket according to an embodiment of the present application, the first buckling structure comprises a first limiting buckle set in the middle of the second side surface of the needle grooved plate and a first elastic buckle set in the middle of the mounting plate, wherein a through-hole is set in the middle of the mounting plate that connects the first side surface and a second side surface of the mounting plate, and the first elastic buckle is set inside the through-hole, the first elastic buckle has a first buckling position that is engaged with the first limiting buckle and a first operating part that extends out of the second side surface of the mounting plate for releasing engagement between the first buckling position and the first limiting buckle.

In the transperineal puncture guiding bracket according to an embodiment of the present application, the second buckling structure comprises a second elastic buckle set at the upper portion of the needle grooved plate, wherein the second elastic buckle has a second buckling position for pressing a top surface of the cover plate and a second operating part for releasing the second buckling position from pressing the top surface of the cover plate.

In the transperineal puncture guiding bracket according to an embodiment of the present application, the second buckling structure comprises a second elastic buckle set at the upper portion of the mounting plate, wherein the second elastic buckle has a second buckling position for pressing a top surface of the cover plate and a second operating part for releasing the second buckling position from pressing the top surface of the cover plate.

In the transperineal puncture guiding bracket according to an embodiment of the present application, the second buckling structure comprises a second limiting buckle set at the upper portion of the first side surface of the needle grooved plate and a second elastic buckle at the corresponding upper portion of the cover plate, wherein a through-hole is set at the upper portion of the cover plate that connects a first side surface and the second side surface of the cover plate, and the second elastic buckle is set inside the through-hole, the second elastic buckle has a second buckling position that is engaged with the second limiting buckle and a second operating part that extends out of the first side surface of the cover plate for releasing engagement between the second buckling position and the second limiting buckle.

In the transperineal puncture guiding bracket according to an embodiment of the present application, the probe fixing assembly comprises an upper fixing member and a lower fixing member, wherein the upper fixing member and the lower fixing member work together to hold outer surface of the intracavitary ultrasound probe, and the mounting plate is set on top of the upper fixing member.

In the transperineal puncture guiding bracket according to an embodiment of the present application, upper wrapping surfaces are formed on a lower surface of the upper fixing member for fitting upper surface of the intracavitary ultrasound probe, and lower wrapping surfaces are formed on an upper surface of the lower fixing member for fitting lower surface of the intracavitary ultrasound probe, and the upper fixing member and the lower fixing member are rotationally connected on one side and buckled on the opposite side to tightly hold the intracavitary ultrasound probe through the upper wrapping surfaces and the lower wrapping surfaces.

Implementing the transperineal puncture guiding bracket of the present application has the following beneficial effects: The transperineal puncture guiding bracket according to the embodiments of the present application can guide puncture needles of different specifications by replacing the guiding assembly with needle holes of different specifications, without a need of replacing the entire transperineal puncture guiding bracket, which facilitates surgical operations of doctors. With the transperineal puncture guiding bracket according to the embodiments of the present application, the puncture needle can be easily separated from the transperineal puncture guiding bracket during surgery by separating the cover plate from the needle grooved plate of the guiding assembly, making the doctor's operation more flexible.

BRIEF DESCRIPTION OF THE DRAWINGS

The present application will be further described with reference to the accompanying drawings and embodiments, in which.

DETAILED DESCRIPTION

To explain objects, technical solutions and advantages of the present application more clearly, the present application will be further described with reference to the accompanying drawings and embodiments in the following. It should be understood that, the specific embodiments described here are only for explanation, but not for limitation to the present application. And, the embodiments and features in the embodiments of the present application can be combined with each other without conflict.

Figure 1:
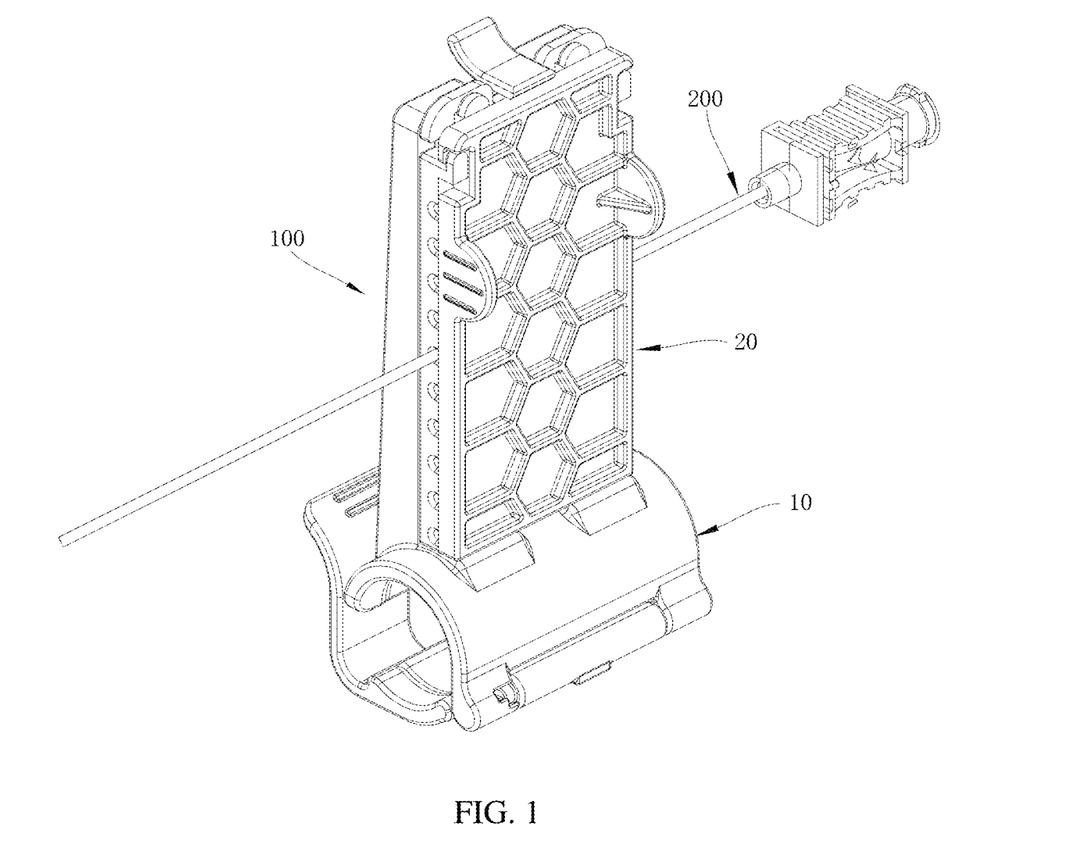
FIG. 1 is a schematic structural diagram of a transperineal puncture guiding bracket according to a first embodiment of the present application.
Figure 2:
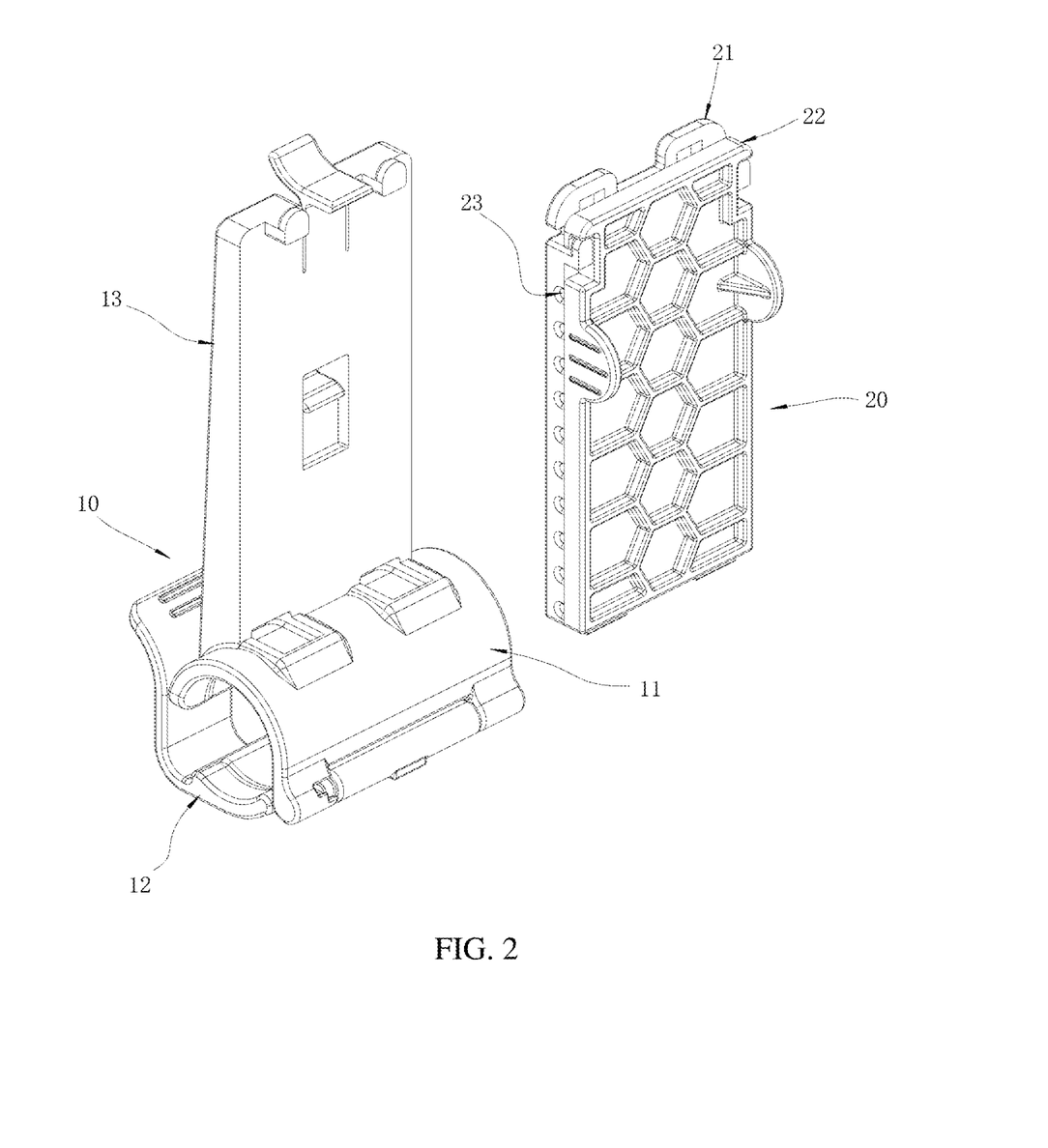
FIG. 2 is an exploded structural diagram of the transperineal puncture guiding bracket shown in FIG. 1.

FIG. 1 shows a schematic structural diagram of a transperineal puncture guiding bracket 100 guiding a puncture needle 200 according to a first embodiment of the present application, and FIG. 2 shows an exploded structural diagram of the transperineal puncture guiding bracket 100. As shown in FIG. 1 and FIG. 2, the transperineal puncture guiding bracket 100 comprises a probe fixing assembly 10 and a guiding assembly 20. The probe fixing assembly 10 is used for fixed installation with an intracavitary ultrasound probe. The guiding assembly 20 is detachably installed on the probe fixing assembly 10. The guiding assembly 20 provides a plurality of needle guiding holes 23 along a puncture direction, which are vertically equidistant and parallel to each other, used to guide the puncture needle 200 to pass through a needle guiding hole 23 for biopsy puncture. The probe fixing assembly 10 further comprises an upper fixing member 11, a lower fixing member 12, and a mounting plate 13. The upper fixing member 11 and the lower fixing member 12 work together to hold outer surface of the intracavitary ultrasound probe for fixation. The mounting plate 13 is set on the upper fixing member 11 for detachable installation of the guiding assembly 20. The guiding assembly 20 further comprises a needle grooved plate 21 and a cover plate 22, which are also detachably combined to form the plurality of vertically equidistant and parallel needle guiding holes 23. The transperineal puncture guiding bracket 100 according to the above embodiment of the present application can guide puncture needles 200 of different specifications by replacing the guiding assembly 20 with needle holes 23 of different specifications, without a need of replacing the entire transperineal puncture guiding bracket 100, which facilitates surgical operations of doctors. With the transperineal puncture guiding bracket 100 according to the above embodiment of the present application, the puncture needle 200 can be easily separated from the transperineal puncture guiding bracket 100 during surgery by separating the cover plate 22 from the needle grooved plate 21 of the guiding assembly 20, making the doctor's operation more flexible.

Figure 3:
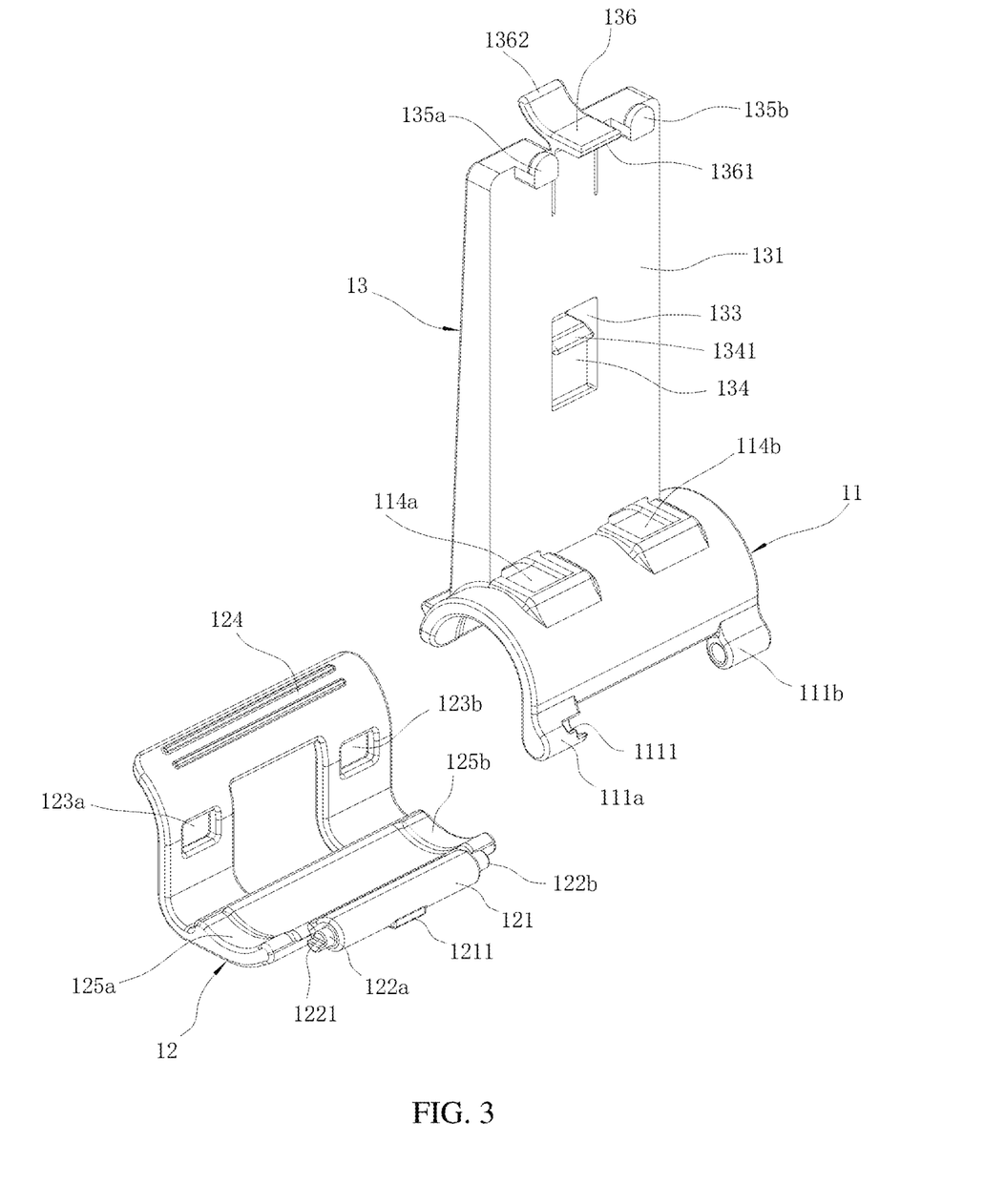
FIG. 3 is an exploded structural diagram of a probe fixing assembly shown in FIG. 2.
Figure 4:
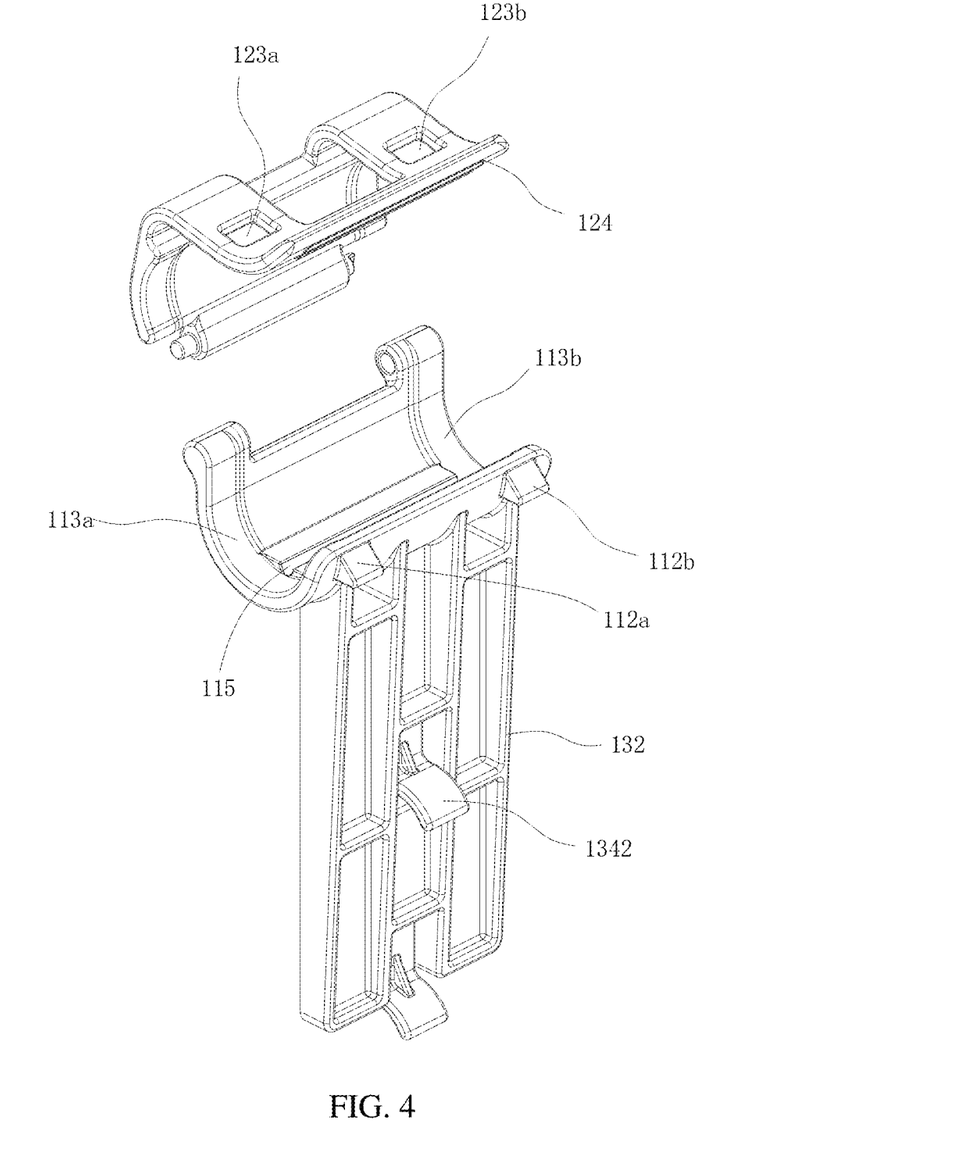
FIG. 4 is an exploded structural diagram of the probe fixing assembly shown in FIG. 2 from another perspective.

FIG. 3 and FIG. 4 respectively show exploded structural diagrams of the probe fixing assembly 10 from different perspectives. As shown in FIG. 3 and FIG. 4, the probe fixing assembly 10 comprises the upper fixing member 11, the lower fixing member 12, and the mounting plate 13. The upper fixing member 11 has a roughly arc shaped outer contour that matches the outer surface of the intracavitary ultrasound probe. The mounting plate 13 is fixedly set on one side along the puncture direction on top of the upper fixing member 11, and can be integrated molded with the upper fixing member 11. A positioning groove 115 that matches a positioning convex bar on the intracavitary ultrasound probe is formed on a lower surface of the upper fixing member 11. Rotation of the upper fixing member 11 can be restricted by aligning and inserting the positioning groove 115 with the positioning convex bar on the intracavitary ultrasound probe. Upper wrapping surfaces 113a and 113b are formed on front and rear ends along the puncture direction of the lower surface of the upper fixing member 11 respectively, which are used for fitting the upper surface of the intracavitary ultrasound probe. In addition, there are shaft sleeves 111a and 111b at the front and rear ends on one side of the upper fixing member 11, and a notch 1111 is formed at an inlet end of one shaft sleeve 111a. On the other side opposite to the two shaft sleeves 111a and 111b of the upper fixing member 11, there are also equipped with two limiting buckles 112a and 112b that are spaced forward and backward. Correspondingly, the lower fixing member 12 also has a roughly arc shaped outer contour that matches the outer surface of the intracavitary ultrasound probe. Two lower wrapping surfaces 125a and 125b are formed at front and rear ends of the upper surface of the lower fixing member 12 respectively, which are fitted with the outer surface of the intracavitary ultrasound probe. In addition, a connecting rod 121 is formed on the lower fixing member 12 on one side corresponding to the two shaft sleeves 111a and 111b of the upper fixing member 11, and two rotating shafts 122a and 122b that rotationally fit with the two shaft sleeves 111a and 111b extend coaxially from both ends of the connecting rod 121. A semi-cylindrical protrusion 1221 is provided at the end of the rotating shaft 122a corresponding to the shaft sleeve 111a having a notch 1111. After the rotating shaft 122b of the lower fixing member 12 is aligned with and inserted into the shaft sleeve 111b of the upper fixing member 11, the lower fixing member 12 is rotated so as to align and insert the semi-cylindrical protrusion 1221 on the rotating shaft 122a into the notch 1111 on the shaft sleeve 111a of the upper fixing member 11, then the lower fixing member 12 is further rotated around the rotating shafts 122a and 122b till an indicator protrusion 1211 on the connecting rod 121 turns to the outside, thus the upper fixing member 11 and the lower fixing member 12 are rotationally connected on the one side (see FIG. 2). On the other side of the lower fixing member 12, a handheld unit 124 extends upwards from the lower fixing member 12, and two retaining rings 123a and 123b are formed on the handheld unit 124, to match the two limiting buckles 112a and 112b on the corresponding other side of the upper fixing member 11. After the upper wrapping surfaces 113a and 113b of the upper fixing member 11 are tightly attached to the upper surface of the intracavitary ultrasound probe with the positioning convex bar on the upper surface of the intracavitary ultrasound probe being aligned and embedded into the positioning groove 115, the lower fixing member 12 is rotated by the handheld unit 124 around axis of the rotating shafts 122a and 122b relative to the upper fixing member 11, till the lower wrapping surfaces 125a and 125b of the lower fixing member 12 are tightly attached to the lower surface of the intracavitary ultrasound probe. Then, the two retaining rings 123a and 123b are interlocked with the two limiting buckles 112a and 112b by force acting on the handheld unit 124 to make the handheld unit 124 generating elastic deformation adapting to the shape of the intracavitary ultrasound probe, thus the upper fixing member 11 and the lower fixing member are clasped on the corresponding other side to tightly hold the intracavitary ultrasound probe. By reverse force acting on the handheld unit 124, the two retaining rings 123a and 123b on the handheld unit 124 can be released from the two limiting buckles 112a and 112b, and then the intracavitary ultrasound probe can be separated by reversibly rotating the lower fixing member 12. Due to a certain deformation curvature of the handheld unit 124, it can withstand clamping forces of different deformation amounts, and therefore the probe fixing assembly 10 can be compatible with intracavitary ultrasound probes with different diameters within a certain range. Moreover, there is avoidance design that does not contact with the intracavitary ultrasound probe between the respective upper wrapping surfaces 113a and 113b of the upper fixing member 11 and the respective lower wrapping surfaces 125a and 125b of the lower fixing member 12. Thus warping of the probe fixing assembly can be avoided after installation on the intracavitary ultrasound probe.

Again as shown in FIG. 3 and FIG. 4, the mounting plate 13 is fixedly set on one side along the puncture direction on top of the upper fixing member 11, having a first side surface 131 and a second side surface 132 opposite to the first side surface 131. There is a through-hole 133 in the middle of the mounting plate 13 that connects the first side surface 131 and the second side surface 132, and a first elastic buckle 134 is set in the through-hole 133 for clamping the needle grooved plate 21 of the guiding assembly 20. The first elastic buckle 134 has a first buckling position 1341 extending out from the first side surface 131 and a first operating part 1342 extending out from the second side surface 132. A second elastic buckle 136 is set in the middle on top of the mounting plate 13, which is used for clamping the cover plate 22 of the guiding assembly 20. According to different embodiments of the present application, the second elastic buckle 136 can also be set at other positions on upper portion of the mounting plate 13, not limited to the top of the mounting plate 13 in the illustrated embodiment. The second elastic buckle 136 also has a second buckling position 1361 extending out from the first side surface 131 and a second operating part 1362 extending out from the second side surface 132. The mounting plate 13 is also equipped with two first hooks 135a and 135b on its first side surface 131, which extend out from the first side surface 131 at front and rear ends on the top of the first side surface 131 respectively, for hanging the needle grooved plate 21 of the guiding assembly 20. Similarly, according to different embodiments of the present application, the first hooks 135a and 135b may also be provided at other positions on the upper portion of the mounting plate 13, not limited to the top of the mounting plate 13 in the illustrated embodiment. There are also two limiting grooves 114a and 114b on the top of the upper fixing member 11 adjacent to the mounting plate 13, which are used to install and position the needle grooved plate 21 of the guiding assembly 20 in cooperation with the mounting plate 13. Regarding specific implementation of the detachable combination structure between the mounting plate 13 and the guiding assembly 20, a more detailed description will be provided in conjunction with the description of the guiding assembly 20 in the below.

Figure 5:
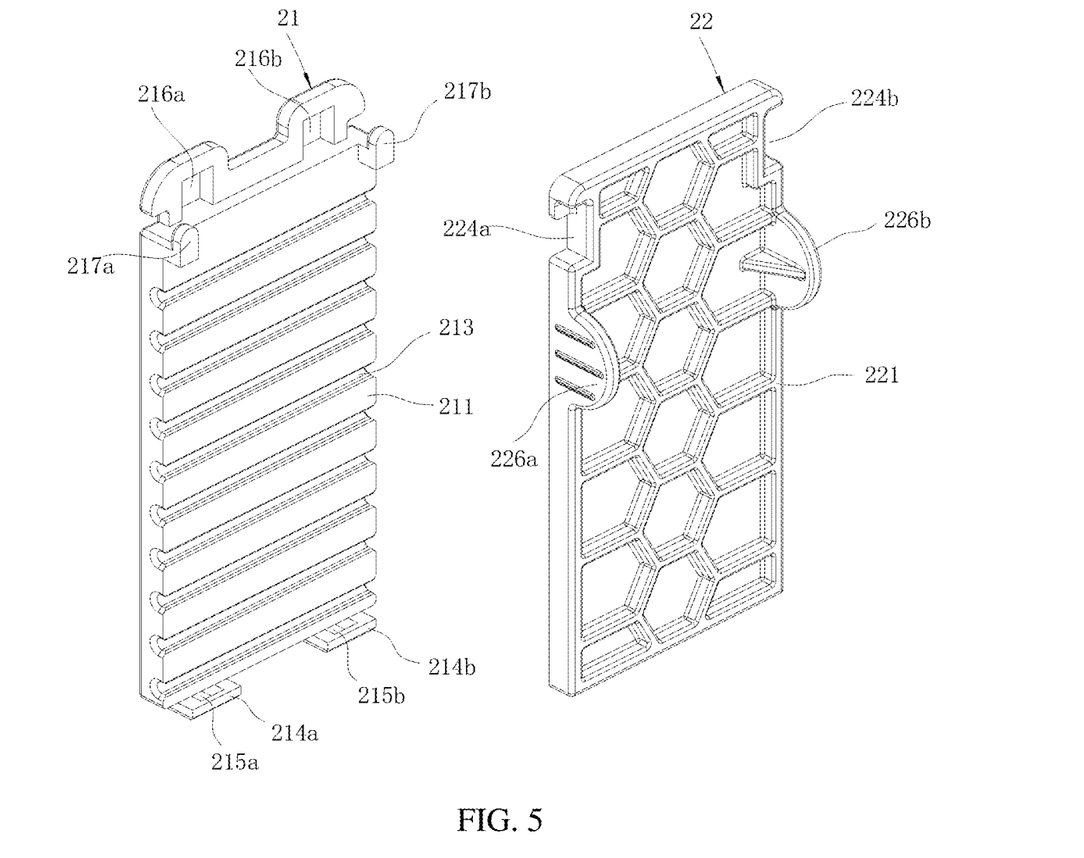
FIG. 5 is an exploded structural diagram of a guiding assembly shown in FIG. 2.
Figure 6:
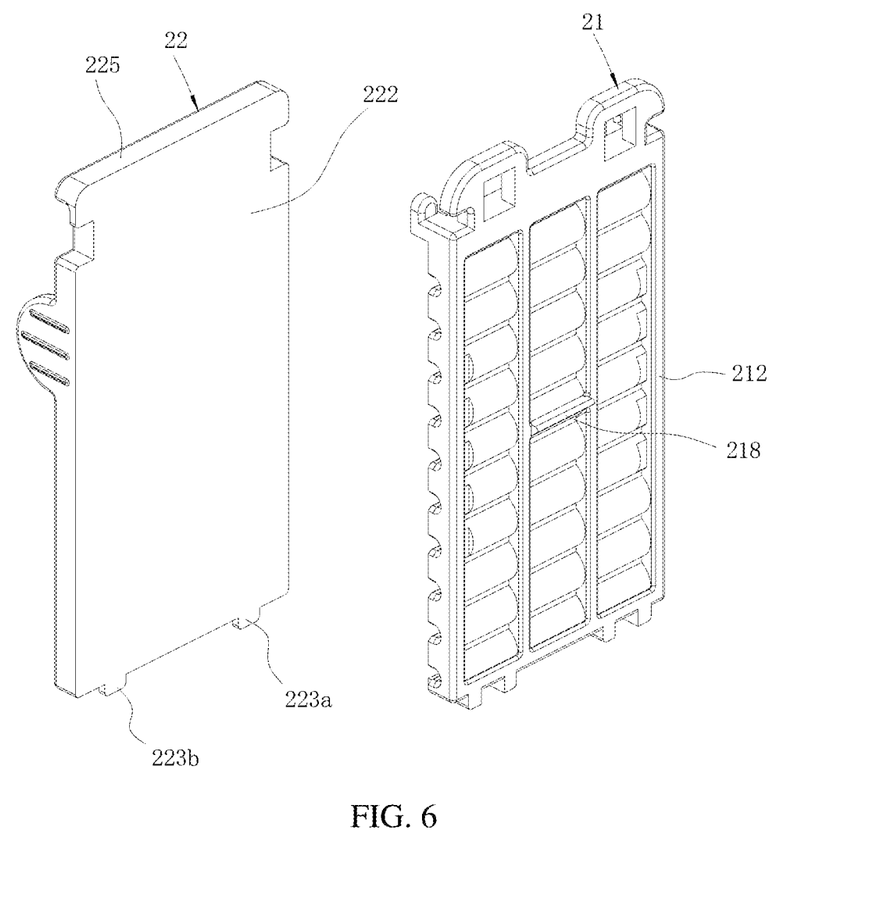
FIG. 6 is an exploded structural diagram of the guiding assembly shown in FIG. 2 from another perspective.
Figure 7:
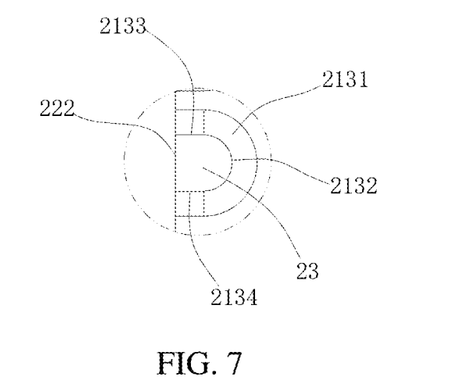
FIG. 7 is a planar structural diagram of a needle inlet end of a needle guiding hole according to the first embodiment of the present application.

FIG. 5 and FIG. 6 show exploded structural diagrams of the guiding assembly 20 from different perspectives respectively. As shown in FIG. 5 and FIG. 6, the guiding assembly 20 is composed of a needle grooved plate 21 and a cover plate 22 that are detachably combined with each other. The needle grooved plate 21 has a first side surface 211 and a second side surface 212 opposite to the first side surface 211. On the first side surface 211 of the needle grooved plate 21, there are a plurality of needle guiding grooves 213 which are vertically equidistant and parallel to each other. The needle guiding grooves 213 pass through the front and rear ends of the needle grooved plate 21 along the puncture direction, and an insertion guiding surface 2131 is formed at least at the needle inlet end (as shown in FIG. 7) to facilitate needle insertion. The insertion guiding surface 2131 is preferably a guiding slope. The cover plate 22 has a first side surface 221 and a second side surface 222 opposite to the first side surface 221. After the cover plate 22 is combined with the needle grooved plate 21, the second side surface 222 of the cover plate 22 is tightly adhered to the first side surface 211 of the needle grooved plate 21, closing open sides of the plurality of needle guiding grooves 213 to form the plurality of needle guiding holes 23. As shown in FIG. 7, each of the needle guiding grooves 213 is preferably a U-shaped groove, which has a half-circle right limiting cambered surface 2132, an upper limiting plat surface 2133, and a lower limiting plat surface 2134 when viewed from the puncture direction, plus the second side surface 222 of the cover plate 22 serving as a left limiting plat surface to form a D-shaped needle guiding hole 23, which limits position of the puncture needle 200 up, down, left, and right, so that the puncture needle 200 can only move axially.

As shown in FIG. 5 and FIG. 6 again, two first limiting feet 214a and 214b are provided at a lower portion (preferably at the bottom) of the needle grooved plate 21, which extend out from the first side surface 211 at front and rear ends of the needle grooved plate 21 respectively, for insertion into the limiting grooves 114a and 114b on top of the upper fixing member 11. There are further limiting holes 215a and 215b on the two first limiting feet 214a and 214b respectively, for insertion and installation of two second limiting feet 223a and 223b provided at a corresponding lower portion (preferably at the bottom) of the cover plate 22. Two second hooks 217a and 217b are provided at an upper portion of the needle grooved plate 21, which extend out from the first side surface 211 at the front and rear ends of the needle grooved plate 21 respectively. Corresponding to the second hooks 217a and 217b, two second hanging holes 224a and 224b are formed at the front and rear ends of the cover plate 22, which are used for hanging the second hooks 217a and 217b. After the second hanging holes 224a and 224b of the cover plate 22 are aligned and hung with the second hooks 217a and 217b of the needle grooved plate 21, the second limiting feet 223a and 223b at the bottom of the cover plate 22 are inserted into the limiting holes 215a and 215b on the first limiting feet 214a and 214b at the bottom of the needle grooved plate 21 by moving downwards the cover plate 22 with its second side surface 222 closely contacting the first side surface 211 of the needle grooved plate 21, thus the cover plate 22 is combined with the needle grooved plate 21. Reverse operation can also separate the cover plate 22 from the needle grooved plate 21. In addition, two first hanging holes 216a and 216b spaced back and forth are formed at the upper portion of the needle grooved plate 21, which pass through the first side surface 211 to the second side surface 212 of the needle grooved plate 21. These two first hanging holes 216a and 216b are matched with the two first hooks 135a and 135b at the top of the mounting plate 13, for the two first hooks 135a and 135b to be hung in. A first limiting buckle 218 is also formed in the middle of the second side surface 212 of the needle grooved plate 21, which is used to engage with the first elastic buckle 134 of the mounting plate 13. On the first side surface 221 of the cover plate 22, there are also two handheld members 226a and 226b extending out from the first side surface 221 at the front and rear ends of the cover plate 22, which are convenient for operation. A process of installing the guiding assembly 20 composed of the combined needle grooved plate 21 and the cover plate 22 onto the probe fixing assembly 10 is as follows: pressing the second operating part 1362 of the second elastic buckle 136 at the top of the mounting plate 13 to lift the second buckling position 1361 of the second elastic buckle 136; then, aligning and hanging the first hanging holes 216a and 216b on the upper portion of the needle grooved plate 21 with the first hooks 135a and 135b on the top of the mounting plate 13, and moving downwards the needle grooved plate 21 with the second side surface 212 of the needle grooved plate 21 being closely attached to the first side surface 131 of the mounting plate 13, and inserting the first limiting feet 214a and 214b on the lower portion of the needle grooved plate 21 into the limiting grooves 114a and 114b on top of the upper fixing member 11, and engaging the first limiting buckle 218 in the middle of the second side surface 212 of the needle grooved plate 21 with the first elastic buckle 1341 in the middle of the mounting plate 13; and then, release the pressing on the second operating part 1362 of the second elastic buckle 136 at the top of the mounting plate 13 to make the second buckling position 1361 of the second elastic buckle 136 press against a top surface 225 of the cover plate 22. Thus the guiding assembly 20 is installed and positioned on the probe fixing assembly 10. Except that the needle grooved plate 21 is firstly combined with the cover plate 22 and then is installed onto the probe fixing assembly 10 as described above, the transperineal puncture guiding bracket 100 according to the embodiments of the present application may also be configured with the needle grooved plate 21 being firstly assembled with the mounting plate 13 of the probe fixing assembly 10 and then being combined with the cover plate 22.

According to the above embodiment of the present application, the lower portion of the needle grooved plate 21 is detachably combined with the upper fixing member 11 by a first vertical insertion structure composed of the first limiting feet 214a and 214b and the limiting grooves 114a and 114b, the upper portion of the needle grooved plate 21 is detachably hung with the upper portion of the mounting plate 13 by a first handing structure composed of the first hanging hole 216a and 216b and the first hooks 135a and 135b, and the middle portion of the second side surface 212 of the needle grooved plate 21 is detachably buckled with the middle portion of the first side surface 131 of the mounting plate 13 by a first buckling structure composed of the first limiting buckle 218 and the first elastic buckle 134, thereby the second side surface 212 of the needle grooved plate 21 is detachably attached to the first side surface 131 of the mounting plate 13. Wherein, the first vertical insertion structure and the first hanging structure are used in combination to limit a vertical downward and left and right lateral movement of the needle grooved plate 21 relative to the mounting plate 13, ensuring that the second side surface 212 of the needle grooved plate 21 is tightly adhered to the first side surface 131 of the mounting plate 13, and the first buckling structure is used to limit a vertical upward movement of the needle grooved plate 21 relative to the mounting plate 13. According to the above embodiment of the present application, the lower portion of the cover plate 22 is detachably combined with the lower portion of the needle grooved plate 21 by a second vertical insertion structure composed of the second limiting feet 223a and 223b and the limiting holes 215a and 215b on the first limiting feet 214a and 214b, the upper portion of the cover plate 22 is detachably hung with the upper portion of the needle grooved plate 21 by a second hanging structure composed of the second hanging holes 224a and 224b and the second hooks 217a and 217b, and the cover plate 22 is further detachably buckled with the mounting plate 13 by a second buckling structure composed of the top surface 225 of the cover plate 21 and the second elastic buckle 136 on the mounting plate 13, thereby the cover plate 22 is detachably combined with the needle grooved plate 21, with the second side surface 222 of the cover plate 22 being in contact with the first side surface 211 of the needle grooved plate 21 to close the plurality of needle guiding grooves 213 to form the plurality of needle guiding holes 23. Wherein, the second vertical insertion structure and the second hanging structure are used in combination to limit a vertical downward and left and right lateral movement of the cover plate 22 relative to the needle grooved plate 21, ensuring that the second side surface 222 of the cover plate 22 is tightly adhered to the first side surface 211 of the needle grooved plate 21, and the second buckling structure is used to limit a vertical upward movement of the cover plate 22 relative to the needle grooved plate 21. In this way, in the transperineal puncture guiding bracket 100 according to the above embodiment of the present application, not only the guiding assembly 20 and the probe fixing assembly 10 can be detachable and separated, but also the cover plate 22 and the needle grooved plate 21 of the guiding assembly 20 can be detachable and separated, and after being assembled, they can also provide a stable structure to guide the puncture needle 200 to perform precise biopsy.

According to the above embodiment of the present application, the puncture needle 200 can be separated from the transperineal puncture guiding bracket 100. During a puncture surgery, the puncture needle 200 can be easily separated from the transperineal puncture guiding bracket 100 by operations of pressing the second operating part 1362 of the second elastic buckle 136 at the top of the mounting plate 13 to lift the second buckle position 1361 of the second elastic buckle 136 and releasing pressure to the cover plated 22, and then pulling up the cover plate 22 through the handheld members 226a and 226b till the second limiting feet 223a and 223b at the lower portion of the cover plate 22 is removed from the limiting holes 215a and 215b at the lower portion of the needle grooved plate 21, and then detaching the second hanging holes 224a and 224b at the upper portion of the cover plate 22 from the second hooks 217a and 217b of the needle grooved plate 21, and then removing the cover plate 22 laterally.

According to the above embodiment of the present application, the transperineal puncture guiding bracket 100 can be replaced with different needle grooved plates 21 according to puncture needles 200 of different specifications. Firstly, the cover plate 22 can be removed referring to the separation operations as described above. Then the needle grooved plate 21 can be removed by operations of pressing the first operating part 1342 of the first elastic buckle 134 in the middle of the mounting plate 13 to release engagement of the first buckling position 1341 of the first elastic buckle 134 with the limiting buckle 218 of the needle grooved plate 21, and then pulling up the needle grooved plate 21 till the first limiting feet 214a and 214b at the lower portion of the needle grooved plate 21 being removed from the limiting grooves 114a and 114b on top of the upper fixing member 11, and then detaching the first hanging holes 216a and 216b at the upper portion of the needle grooved plate 21 from the first hooks 135a and 135b of the mounting plate 13, and then removing the needle grooved plate 21 laterally. Finally, a new needle grooved plate can be installed to replace the needle grooved plate 21 referring to the installation process of the needle grooved plate 21 mentioned earlier.

Figure 8:
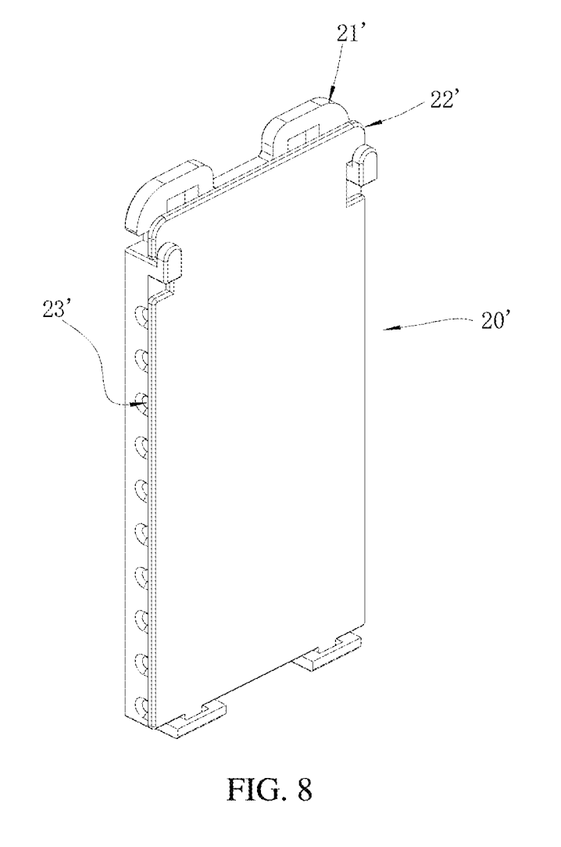
FIG. 8 is a schematic structural diagram of a guiding assembly according to a second embodiment of the present application.

In the transperineal puncture guiding bracket 100 according to the above embodiment of the present application, the needle grooved plate 21 and the cover plate 22 that constitute the guiding assembly 20 are both made of plastic materials with low cost. According to a second embodiment of the present application, as shown in FIG. 8, a guiding assembly 20' can be made of metal materials, comprising a metal needle grooved plate 21' and a metal cover plate 22'. Both of them can be combined with detachable structures that are basically the same as the needle grooved plate 21 and the cover plate 22 of the aforementioned embodiment to form a plurality of parallel and equidistant metal needle guiding holes 23'. A biggest advantage of the metal guiding assembly 20' is that it can prevent the puncture needle from scratching wall of the needle guiding holes 23' and generating debris.

Figure 9:
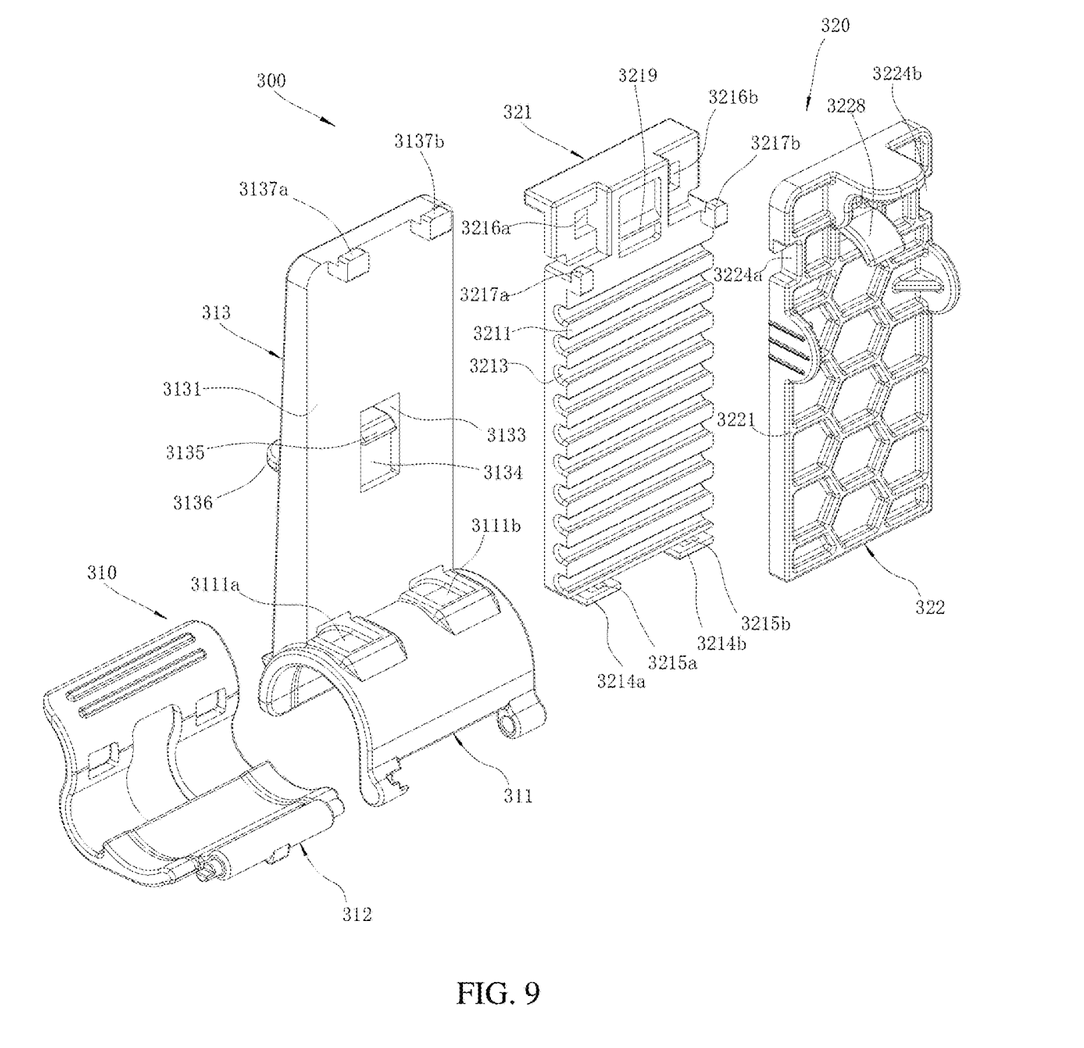
FIG. 9 is an exploded structural diagram of a transperineal puncture guiding bracket according to a third embodiment of the present application.
Figure 10:
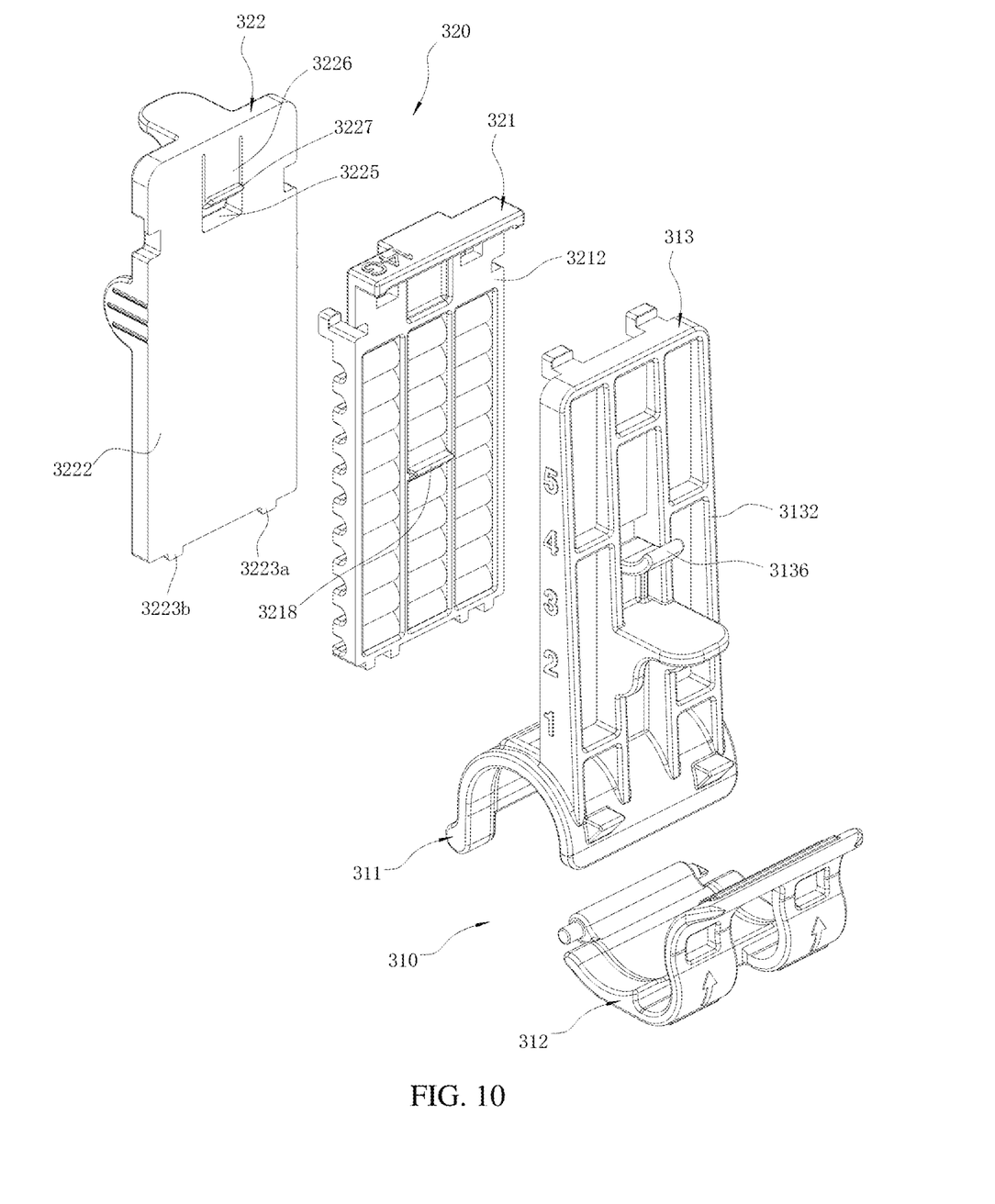
FIG. 10 is an exploded structural diagram of the transperineal puncture guiding bracket shown in FIG. 9 from another perspective.

FIG. 9 and FIG. 10 illustrate exploded structural diagrams of a transperineal puncture guiding bracket 300 according to a third embodiment of the present application respectively. As shown in FIG. 9 and FIG. 10, the transperineal puncture guiding bracket 300 has a similar structure to that of the transperineal puncture guiding bracket 100 in the first embodiment mentioned above, and also comprises a probe fixing assembly 310 and a guiding assembly 320. Similarly, the probe fixing assembly 310 further comprises an upper fixing member 311, a lower fixing member 312, and a mounting plate 313. The upper fixing member 311 and the lower fixing member 312 work together to hold outer surface of the intracavitary ultrasound probe for fixation, and the mounting plate 313 is provided on the upper fixing member 311 for detachable installation of the guiding assembly 320. The guiding assembly 320 further comprises a needle grooved plate 321 and a cover plate 322. The needle grooved plate 321 has a first side surface 3211 and a second side surface 3212 opposite to the first side surface 3211, and the first side surface 3211 of the needle grooved plate 321 is provided with a plurality of vertically equidistant and parallel needle guiding grooves 3213. The cover plate 322 has a first side surface 3221 and a second side surface 3222 opposite to the first side surface 3221. The cover plate 322 is also detachably combined with the needle grooved plate 321 to tightly adhere the second side surface 3222 of the cover plate 322 to the first side surface 3211 of the needle grooved plate 3211, thereby closing open sides of the plurality of needle guiding grooves 3213 to form a plurality of needle guiding holes for guiding the puncture needle to perform biopsy puncture.

As shown in FIG. 9 and FIG. 10, there is a through-hole 3133 in the middle of the mounting plate 313 that connects a first side surface 3131 and a second side surface 3132 of the mounting plate 313, and a first elastic buckle 3134 is set in the through-hole 3133 for clamping the first limiting buckle 3218 in the middle of the second side surface 3212 of the needle grooved plate 21. The first elastic buckle 3134 has a first buckling position 3135 that extends out of the first side surface 3131 and engages with the first limiting buckle 3218, and a first operating part 3136 that extends out of the second side surface 3132 for users to operate and release the engagement between the first buckling position 3135 and the first limiting buckle 3218. The mounting plate 313 is equipped with two first hooks 3137*a* and 3137*b* on its first side surface 3131, which extend out from the first side surface 3131 at front and rear ends at an upper portion (preferably at the top) of the first side surface 3131 respectively, for installation with two first hanging holes 3216*a* and 3216*b* at a corresponding upper portion of the needle grooved plate 321. There are two limiting grooves 3111*a* and 3111*b* on top of the upper fixing member 311 adjacent to the mounting plate 313, which are used for vertical insertion of two first limiting feet 3214*a* and 3214*b* extending out of the first side surface 3211 at the front and rear ends of the needle grooved plate 321 respectively. Furthermore, there are limiting holes 3215*a* and 3215*b* on the two first limiting feet 3214*a* and 3214*b* of the needle grooved plate 321 respectively, for insertion and installation of two second limiting feet 3223*a* and 3223*b* provided at a corresponding lower portion (preferably at the bottom) of the cover plate 322. Two second hooks 3217*a* and 3217*b* are provided at an upper portion of the needle grooved plate 321, which extend out from the first side surface 3211 at the front and rear ends of the needle grooved plate 321 respectively, for hanging with corresponding second hanging holes 3224*a* and 3224*b* at the front and rear ends of the cover plate 322. A difference between the transperineal puncture guiding bracket 300 shown in FIG. 9 and FIG. 10 and the transperineal puncture guiding bracket 100 in the aforementioned first embodiment of the present application is that, a second limiting buckle 3219 is set in the middle of the upper portion of the first side surface 3211 of the needle grooved plate 321, and a through-hole 3225 is opened in the middle of the upper portion of the cover plate 322, which passes through the first side surface 3221 and the second side surface 3222 of the cover plate 322, and a second elastic buckle 3226 is set in the through-hole 3225, which is used to engage with the second limiting buckle 3219 on the first side surface 3211 of the needle grooved plate 321. The second elastic buckle 3226 has a second buckling position 3227 that extends out of the second side surface 3222 and engages with the second limiting buckle 3219, and a second operating part 3228 that extends out of the first side surface 3221 for users to operate and release the engagement between the second buckling position 3227 and the second limiting buckle 3219. In the transperineal puncture guiding bracket 300 according to the third embodiment of the present application, the lower portion of the needle grooved plate 321 is detachably combined with the upper fixing member 311 by a first vertical insertion structure composed of the first limiting feet 3214*a* and 3214*b* and the limiting grooves 3111*a* and 3111*b*, the upper portion of the needle grooved plate 321 is detachably hung with the upper portion of the mounting plate 313 by a first handing structure composed of the first hanging hole 3216*a* and 3216*b* and the first hooks 3137*a* and 3137*b*, and the middle portion of the second side surface 3212 of the needle grooved plate 321 is detachably buckled with the middle portion of the first side surface 3131 of the mounting plate 313 by a first buckling structure composed of the first limiting buckle 3218 and the first elastic buckle 3134, thereby the second side surface 3212 of the needle grooved plate 321 is detachably attached to the first side surface 3131 of the mounting plate 313. The lower portion of the cover plate 322 is detachably combined with the lower portion of the needle grooved plate 321 by a second vertical insertion structure composed of the second limiting feet 3223*a* and 3223*b* and the limiting holes 3215*a* and 3215*b* on the first limiting feet 3214*a* and 3214*b*, the upper portion of the cover plate 322 is detachably hung with the upper portion of the needle grooved plate 321 by a second hanging structure composed of the second hanging holes 3224*a* and 3224*b* and the second hooks 3217*a* and 3217*b*, and the cover plate 322 is further detachably buckled with the first side surface 3211 of the needle grooved plate 321 by a second buckling structure composed of the second elastic buckle 3226 and the second limiting buckle 3219, thereby the cover plate 322 is detachably combined with the needle grooved plate 321, with the second side surface 3222 of the cover plate 322 being in contact with the first side surface 3211 of the needle grooved plate 321 to close the plurality of needle guiding grooves 3213 to form the plurality of needle guiding holes. In this way, in the transperineal puncture guiding bracket 300 according to the third embodiment of the present application, not only the guiding assembly 320 and the probe fixing assembly 310 can be detachable and separated, but also the cover plate 322 and the needle grooved plate 321 of the guiding assembly 320 can be detachable and separated, and after being assembled, they can also provide a stable structure to guide the puncture needle to perform precise biopsy.

Figure 11:
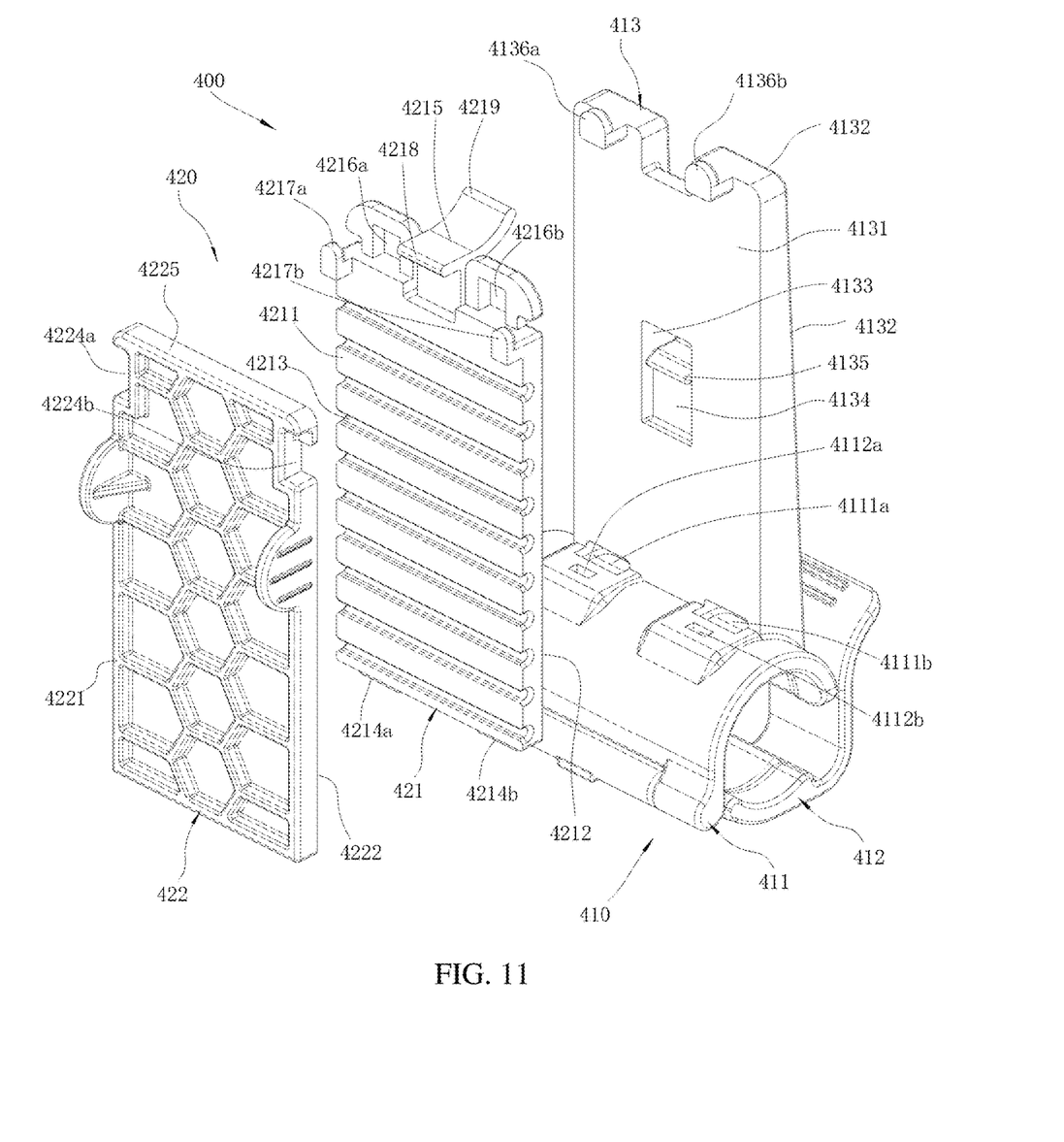
FIG. 11 is schematic structural diagram of a transperineal puncture guiding bracket according to a fourth embodiment of the present application.

FIG. 11 shows an exploded structural diagram of a transperineal puncture guiding bracket 400 according to a fourth embodiment of the present application. As shown in FIG. 11, the transperineal puncture guiding bracket 400 has structure that is basically the same as the transperineal puncture guiding bracket 100 in the first embodiment mentioned above, and also comprises a probe fixing assembly 410 and a guiding assembly 420. Similarly, the probe fixing assembly 410 further comprises an upper fixing member 411, a lower fixing member 412, and a mounting plate 413. The upper fixing member 411 and the lower fixing member 412 work together to hold outer surface of the intracavitary ultrasound probe for fixation. The mounting plate 413 is provided on the upper fixing member 411 for detachable installation of the guiding assembly 420. The guiding assembly 420 further comprises a needle grooved plate 421 and a cover plate 422. The needle grooved plate 421 has a first side surface 4211 and a second side surface 4212 opposite to the first side surface 4211, and the first side surface 4211 of the needle grooved plate 421 is provided with a plurality of vertically equidistant and parallel needle guiding grooves 4213. The cover plate 422 has a first side surface 4221 and a second side surface 4222 opposite to the first side surface 4221. The cover plate 422 is also detachably combined with the needle grooved plate 421 to tightly adhere the second side surface 4222 of the cover plate 422 to the first side surface 4211 of the needle grooved plate 421, thereby closing open sides of the plurality of needle guiding grooves 4213 to form a plurality of needle guiding holes for guiding the puncture needle to perform biopsy puncture.

Further as shown in FIG. 11, a through-hole 4133 is formed in the middle of the mounting plate 413 that connects the first side surface 4131 and the second side surface 4132, and a first elastic buckle 4134 is set in the through-hole 4133 for clamping the first limiting buckle (not visible in the figure) in the middle of the second side surface 4212 of the needle grooved plate 421. The first elastic buckle 4134 has a first buckling position 4135 that extends out of the first side surface 4131 and engages with the first limiting buckle, and a first operating part that extends out of the second side surface 4132 (not visible in the figure) for users to operate and release the engagement between the first buckling position 4135 and the first limiting buckle. The mounting plate 413 is equipped with two first hooks 4136a and 4136b on its first side surface 4131, which extend out from the first side surface 4131 at front and rear ends at an upper portion (preferably at the top) of the first side surface 4131 respectively, for installation with two first hanging holes 4216a and 4216b at a corresponding upper portion of the needle grooved plate 421. There are two first limiting grooves 4111a and 4111b on top of the upper fixing member 411 adjacent to the mounting plate 413, which are used for vertical insertion of two first limiting feet 4214a and 4214b provided at the front and rear ends of the lower portion (preferably at the bottom) of the needle grooved plate 321 respectively. Furthermore, two second hooks 4217a and 4217b are provided at an upper portion of the needle grooved plate 421, which extend out from the first side surface 4211 at the front and rear ends of the needle grooved plate 421 respectively, for hanging with corresponding second hanging holes 4224a and 4224b at the front and rear ends of the cover plate 422. A difference between the transperineal puncture guiding bracket 400 shown in FIG. 11 and the transperineal puncture guiding bracket 100 in the aforementioned first embodiment of the present application is that, there are two second limiting grooves 4112a and 4112b on top of the upper fixing member 411 adjacent the two first limiting grooves 4111a and 4111b respectively, for vertical insertion of two second limiting feet (not visible in the figure) at the front and rear ends of the lower portion (preferably at the bottom) of the cover plate 422. The other difference between the transperineal puncture guiding bracket 400 shown in FIG. 11 and the transperineal puncture guiding bracket 100 in the aforementioned first embodiment of the present application is that, a second elastic buckle 4215 is provided in the middle of the upper portion (preferably the top) of the needle grooved plate 421. The second elastic buckle 4215 has a second buckling position 4218 extending out of the first side surface 4211 and a second operating part 4219 extending out of the second side surface 4212. The second buckling position 4216 of the second elastic buckle 4215 presses against the top surface 4225 of the cover plate 422 to form a detachable buckling installation. By operating the second operating part 4219, buckling by the second buckling position 4216 to the top surface 4225 of the cover plate 322 can be released.

In the transperineal puncture guiding bracket 400 according to the fourth embodiment of the present application, the lower portion of the needle grooved plate 421 is detachably combined with the upper fixing member 411 by a first vertical insertion structure composed of the first limiting feet 4214a and 4214b and the first limiting grooves 4111a and 4111b, the upper portion of the needle grooved plate 421 is detachably hung with the upper portion of the mounting plate 413 by a first handing structure composed of the first hanging hole 4216a and 4216b and the first hooks 4136a and 4136b, and the middle portion of the second side surface 4212 of the needle grooved plate 421 is detachably buckled with the middle portion of the first side surface 4131 of the mounting plate 413 by a first buckling structure composed of the first limiting buckle (not visible in the figure) and the first elastic buckle 4134, thereby the second side surface 4212 of the needle grooved plate 421 is detachably attached to the first side surface 4131 of the mounting plate 413. The lower portion of the cover plate 422 is detachably combined with the lower portion of the needle grooved plate 421 by a second vertical insertion structure composed of the second limiting feet (not visible in the figure) and the second limiting grooves 4112a and 4112b, the upper portion of the cover plate 422 is detachably hung with the upper portion of the needle grooved plate 421 by a second hanging structure composed of the second hanging holes 4224a and 4224b and the second hooks 4217a and 4217b, and the upper portion of the cover plate 422 is further detachably buckled with the needle grooved plate 421 by a second buckling structure composed of the top surface 4225 of the cover plate 422 and the second elastic buckle 4215 of the needle grooved plate 421, thereby the cover plate 422 is detachably combined with the needle grooved plate 421, with the second side surface 4222 of the cover plate 422 being in contact with the first side surface 4211 of the needle grooved plate 421 to close the plurality of needle guiding grooves 4213 to form the plurality of needle guiding holes. In this way, in the transperineal puncture guiding bracket 400 according to the fourth embodiment of the present application, not only the guiding assembly 420 and the probe fixing assembly 410 can be detachable and separated, but also the cover plate 422 and the needle grooved plate 421 of the guiding assembly 420 can be detachable and separated, and after being assembled, they can also provide a stable structure to guide the puncture needle to perform precise biopsy.

The above is only the preferred embodiments of the present application, and is not intended to limit the present application. Any modifications, equivalent substitutions and improvements made within the spirit and principles of the present application should be included within the protection scope of the present application.

We claim:

1. A transperineal puncture guiding bracket, comprising a probe fixing assembly and a guiding assembly, wherein the probe fixing assembly is fixedly installed with an intracavitary ultrasound probe, the guiding assembly provides a plurality of vertically distributed and parallel needle guiding holes along a puncture direction, characterized in that, a mounting plate is set on top of the probe fixing assembly, and the guiding assembly further comprises a needle grooved plate and a cover plate, the needle grooved plate has a first side surface and a second side surface opposite to the first side surface, with the first side surface of the needle grooved plate being provided with a plurality of vertically distributed and parallel needle guiding grooves; and a lower portion of the needle grooved plate is detachably combined with the top of the probe fixing assembly adjacent to the mounting plate by a first vertical insertion structure, an upper portion of the needle grooved plate is detachably hung with an upper portion of the mounting plate by a first hanging structure, and the second side surface of the needle grooved plate is detachably buckled with a first side surface of the mounting plate by a first buckling structure, thereby the second side surface of the needle grooved plate is detachably attached to the first side surface of the mounting plate; and a lower portion of the cover plate is detachably combined with the lower portion of the needle grooved plate or the top of the probe fixing assembly by a second vertical insertion structure, an upper portion of the cover plate is detachably hung with the upper portion of the needle grooved plate by a second hanging structure, and the cover plate is further detachably buckled with the upper portion of the mounting plate, the upper portion of the needle grooved plate or the top of the probe fixing assembly through a second buckling structure, thereby a second side surface of the cover plate is detachably attached to the first side surface of the needle grooved plate to close the plurality of needle guiding grooves to form the plurality of needle guiding holes.

2. The transperineal puncture guiding bracket of claim 1, characterized in that the first vertical insertion structure comprises first limiting feet provided at the lower portion of the needle grooved plate which extend out from the first side surface of the needle grooved plate and limiting grooves formed at the top of the probe fixing assembly for insertion of the first limiting feet; and the second vertical insertion structure comprises second limiting feet set at the lower portion of the cover plate and limiting holes on the first limiting feet of the needle grooved plate for insertion of the second limiting feet.

3. The transperineal puncture guiding bracket of claim 1, characterized in that the first vertical insertion structure comprises first limiting feet provided at the lower portion of the needle grooved plate and first limiting grooves set at the top of the probe fixing assembly for insertion of the first limiting feet; and the second vertical insertion structure comprises second limiting feet set at the lower portion of the cover plate and second limiting grooves formed at the top of the probe fixing assembly for insertion of the second limiting feet.

4. The transperineal puncture guiding bracket of claim 1, characterized in that the first hanging structure comprises first hanging holes at the upper portion of the needle grooved plate and first hooks at the upper portion of the mounting plate which extend out from the first side surface of the mounting plate to hang into the first hanging holes; and the second hanging structure comprises second hanging holes at the upper portion of the cover plate and second hooks at the upper portion which extend out from the first side surface of the needle grooved plate to hang into the second hanging holes.

5. The transperineal puncture guiding bracket of claim 1, characterized in that the first buckling structure comprises a first limiting buckle set in the middle of the second side surface of the needle grooved plate and a first elastic buckle set in the middle of the mounting plate, wherein a through-hole is set in the middle of the mounting plate that connects the first side surface and a second side surface of the mounting plate, and the first elastic buckle is set inside the through-hole, the first elastic buckle has a first buckling position that is engaged with the first limiting buckle and a first operating part that extends out of the second side surface of the mounting plate for releasing engagement between the first buckling position and the first limiting buckle.

6. The transperineal puncture guiding bracket of claim 1, characterized in that the second buckling structure comprises a second elastic buckle set at the upper portion of the needle grooved plate, wherein the second elastic buckle has a second buckling position for pressing a top surface of the cover plate and a second operating part for releasing the second buckling position from pressing the top surface of the cover plate.

7. The transperineal puncture guiding bracket of claim 1, characterized in that the second buckling structure comprises a second elastic buckle set at the upper portion of the mounting plate, wherein the second elastic buckle has a second buckling position for pressing a top surface of the cover plate and a second operating part for releasing the second buckling position from pressing the top surface of the cover plate.

8. The transperineal puncture guiding bracket of claim 1, characterized in that the second buckling structure comprises a second limiting buckle set at the upper portion of the first side surface of the needle grooved plate and a second elastic buckle at the corresponding upper portion of the cover plate, wherein a through-hole is set at the upper portion of the cover plate that connects a first side surface and the second side surface of the cover plate, and the second elastic buckle is set inside the through-hole, the second elastic buckle has a second buckling position that is engaged with the second limiting buckle and a second operating part that extends out of the first side surface of the cover plate for releasing engagement between the second buckling position and the second limiting buckle.

9. The transperineal puncture guiding bracket of claim 1, characterized in that the probe fixing assembly comprises an upper fixing member and a lower fixing member, wherein the upper fixing member and the lower fixing member work together to hold outer surface of the intracavitary ultrasound probe, and the mounting plate is set on top of the upper fixing member.

10. The transperineal puncture guiding bracket of claim 9, characterized in that upper wrapping surfaces are formed on a lower surface of the upper fixing member for fitting upper surface of the intracavitary ultrasound probe, and lower wrapping surfaces are formed on an upper surface of the lower fixing member for fitting lower surface of the intracavitary ultrasound probe, and the upper fixing member and the lower fixing member are rotationally connected on one side and buckled on the opposite side to tightly hold the intracavitary ultrasound probe through the upper wrapping surfaces and the lower wrapping surfaces.

\* \* \* \* \*